US009848764B2

(12) United States Patent
Dextradeur et al.

(10) Patent No.: US 9,848,764 B2
(45) Date of Patent: Dec. 26, 2017

(54) FLUID MANAGEMENT CATHETER AND METHODS OF USING SAME

(71) Applicant: INTEGRA LIFESCIENCES SWITZERLAND SÀRL, Le Locle (CH)

(72) Inventors: Alan J. Dextradeur, Franklin, MA (US); Daniel McCusker, Bridgewater, MA (US)

(73) Assignee: INTEGRA LIFESCIENCES SWITZERLAND SÀRL, Le Locle (CH)

(*) Notice: Subject to any disclaimer, the term of this patent is extended or adjusted under 35 U.S.C. 154(b) by 0 days.

(21) Appl. No.: 14/513,692

(22) Filed: Oct. 14, 2014

(65) Prior Publication Data

US 2015/0031956 A1    Jan. 29, 2015

Related U.S. Application Data

(62) Division of application No. 13/427,232, filed on Mar. 22, 2012, now abandoned.

(51) Int. Cl.
*A61M 27/00* (2006.01)
*A61N 5/06* (2006.01)
(Continued)

(52) U.S. Cl.
CPC .......... *A61B 1/313* (2013.01); *A61B 1/00165* (2013.01); *A61B 1/015* (2013.01);
(Continued)

(58) Field of Classification Search
CPC .............. A61M 25/00; A61M 25/0067; A61M 25/0068; A61M 25/007; A61M 25/0074;
(Continued)

(56) References Cited

U.S. PATENT DOCUMENTS 4,757,381 A   7/1988   Cooper
4,759,762 A   7/1988   Grendahl
(Continued)

FOREIGN PATENT DOCUMENTS

JP   11056758 A      3/1999
JP   2003507140 A   2/2003
(Continued)

OTHER PUBLICATIONS

Medtronic PS Medical; Medtronic PS Medical NeuroPEN Endocope and Optical Accessories Safety and effectiveness Summary; Feb. 22, 2001; Goleta, CA.

*Primary Examiner* — Ryan Henderson
(74) *Attorney, Agent, or Firm* — Troutman Sanders LLP

(57) ABSTRACT

A catheter and method for managing fluid in a patient, the catheter having an elongated shaft with a distal end and a proximal end. The shaft defines at least one lumen extending substantially therethrough, the shaft further defining a plurality of drainage holes along a distal portion of the shaft, with the drainage holes in fluid communication with the lumen. The catheter further has a substantially transparent tip portion attached to the distal end of the shaft with an outer distal leading surface that is substantially rounded to assist insertion through tissue.

6 Claims, 3 Drawing Sheets

(51) Int. Cl.

| | | |
|---|---|---|
| *A61B 1/015* | (2006.01) | |
| *A61M 25/00* | (2006.01) | |
| *A61B 18/24* | (2006.01) | |
| *A61B 1/00* | (2006.01) | |
| *A61B 18/18* | (2006.01) | |
| *A61B 18/20* | (2006.01) | |
| *A61B 18/22* | (2006.01) | |
| *A61B 18/00* | (2006.01) | |
| *A61B 1/313* | (2006.01) | |

(52) U.S. Cl.
CPC .......... *A61B 18/24* (2013.01); *A61M 25/007* (2013.01); *A61M 25/0068* (2013.01); *A61M 25/0069* (2013.01); *A61M 27/00* (2013.01); *A61M 27/006* (2013.01); *A61N 5/0601* (2013.01); *A61N 5/0603* (2013.01); *A61B 2018/00446* (2013.01); *A61B 2018/00982* (2013.01); *A61B 2018/1807* (2013.01); *A61B 2018/2005* (2013.01); *A61B 2018/2261* (2013.01); *A61B 2218/002* (2013.01); *A61M 2027/004* (2013.01); *A61M 2210/0693* (2013.01); *A61N 2005/0612* (2013.01)

(58) Field of Classification Search
CPC .......... A61M 25/0075; A61M 25/0076; A61M 25/0078; A61M 27/00; A61M 27/002; A61M 27/006; A61M 1/008; A61M 1/0084; A61M 2210/0693; A61B 1/12; A61B 1/128; A61B 1/00163; A61B 1/00165; A61B 1/00167; A61B 1/0017; A61B 1/313; A61B 18/24; A61B 2018/1807; A61B 2018/2005; A61B 2018/0046; A61B 2018/00982; A61B 2018/002; A61B 2018/2261; A61N 5/0601; A61N 5/0603; A61N 5/0612
USPC ........ 600/104–107, 114, 115, 121–125, 127, 600/129, 156–159, 175; 604/23, 26, 604/43–45, 506–508, 514, 516; 606/185, 606/190
See application file for complete search history.

(56) References Cited

U.S. PATENT DOCUMENTS

| | | |
|---|---|---|
| 5,041,109 A | 8/1991 | Abela |
| 5,152,788 A | 10/1992 | Isaacson |
| 5,237,984 A | 8/1993 | Williams, III |
| 5,263,928 A | 11/1993 | Trauthen |
| 5,402,768 A | 4/1995 | Adair |
| 5,437,626 A | 8/1995 | Cohen |
| 5,458,606 A | 10/1995 | Cohen |
| 5,690,117 A * | 11/1997 | Gilbert ............ A61B 1/05 600/342 |
| 5,693,043 A | 12/1997 | Kittrell |
| 5,738,666 A | 4/1998 | Watson |
| 5,782,825 A | 7/1998 | Anderson |
| 5,951,464 A | 9/1999 | Takahashi |
| RE36,434 E | 12/1999 | Hamlin |
| 6,045,530 A * | 4/2000 | Krueger et al. ........ 604/95.04 |
| 6,231,514 B1 | 5/2001 | Lowe |
| 6,953,457 B2 | 10/2005 | Farr |
| 7,351,253 B2 | 4/2008 | DiMauro |
| 7,389,776 B2 | 6/2008 | Maksimovich |
| 7,396,354 B2 | 7/2008 | Rychnovsky |
| 7,490,612 B2 | 2/2009 | Maksimovich |
| 7,527,594 B2 | 5/2009 | Vardi |
| 7,591,780 B2 | 9/2009 | Jacobsen |
| 7,711,413 B2 | 5/2010 | Feldman |
| 7,734,332 B2 | 6/2010 | Sher |
| 7,758,499 B2 | 7/2010 | Adler |
| 7,860,555 B2 | 12/2010 | Saadat |
| 7,918,787 B2 | 4/2011 | Saadat |
| 7,922,654 B2 | 4/2011 | Boutillette |
| 7,935,060 B2 | 5/2011 | Schmitt |
| 2005/0251116 A1 | 11/2005 | Steinke |
| 2005/0288622 A1* | 12/2005 | Albrecht et al. ............ 604/23 |
| 2008/0039768 A1 | 2/2008 | Francis |
| 2008/0086074 A1 | 4/2008 | Taylor |
| 2008/0119739 A1 | 5/2008 | Vardi |
| 2008/0177138 A1 | 7/2008 | Courtney |
| 2008/0221458 A1 | 9/2008 | Scott |
| 2008/0243002 A1 | 10/2008 | Munce |
| 2008/0243031 A1 | 10/2008 | Seibel |
| 2008/0275304 A1 | 11/2008 | Barbato |
| 2009/0043191 A1 | 2/2009 | Castella |
| 2009/0054955 A1 | 2/2009 | Kopell |
| 2009/0112198 A1 | 4/2009 | Khanna |
| 2009/0163900 A1 | 6/2009 | Taylor |
| 2009/0281500 A1 | 11/2009 | Acosta |
| 2009/0287048 A1 | 11/2009 | Jacobson |
| 2009/0318759 A1 | 12/2009 | Jacobsen |
| 2009/0326328 A1 | 12/2009 | Kucklick |
| 2010/0081988 A1 | 4/2010 | Kahle |
| 2010/0286585 A1 | 11/2010 | Dimauro |

FOREIGN PATENT DOCUMENTS

| | | | | |
|---|---|---|---|---|
| JP | 2006314744 A | * | 11/2006 | ............ A61B 1/00 |
| WO | WO 0074613 A1 | | 12/2000 | |
| WO | WO 0113984 A2 | | 3/2001 | |
| WO | WO 0209610 A1 | | 2/2002 | |

* cited by examiner

FLUID MANAGEMENT CATHETER AND METHODS OF USING SAME

CROSS REFERENCE TO RELATED APPLICATION

The present application is a divisional of U.S. patent application Ser. No. 13/427,232, filed Mar. 22, 2012.

BACKGROUND OF THE INVENTION

1. Field of the Invention

The invention relates to a device and methods for managing bodily fluids in a patient and more particularly to an implantable catheter having an optically useful tip.

2. Description of the Related Art

There are a number of conditions in patients for which it is desirable to add or withdraw fluid. Some fluid management conditions involve the mammalian brain. Within the cranium, gray and white matter is suspended in cerebrospinal fluid and nourished by blood delivered through cerebral arteries. The gray matter has closely spaced cell bodies of neurons, such as in the cerebral cortex, and the underlying white matter contains densely packed axons that transmit signals to other neurons. Human brain tissue has different densities and comprises approximately eighty percent of the intracranial content, with blood and cerebrospinal fluid each normally comprising approximately ten percent.

Cerebrospinal fluid is produced in several connected chambers known as ventricles and typically is renewed four to five times per day. Cerebrospinal fluid in a healthy human flows slowly and continuously through the ventricles, propelled by pulsations of the cerebral arteries. The fluid flows around the brain tissues and the spinal column, and then through small openings into the arachnoid membrane, which is the middle layer of the meninges surrounding the brain parenchyma and ventricles, where the fluid is finally reabsorbed into the bloodstream.

Under normal conditions, bodily mechanisms compensate for a change in fluid volume within the cranium through tissue resilience and by adjusting the total volume of blood and cerebrospinal fluid so that a small increase in fluid volume does not increase intracranial pressure. Similarly, a healthy brain compensates for an increase in intracranial pressure to minimize a corresponding increase in intracranial volume. This volume- and pressure-relationship can be explained in terms of cerebral compliance, which term is intended to include herein the terms elastance and intracranial compliance.

The brain is compliant as long as a person's auto-regulatory mechanism can compensate for any change in volume. As soon as the brain's auto-regulation or compensatory mechanisms fail, blood and cerebrospinal fluid cannot be displaced, and the brain can no longer adapt to any increase in fluid volume. A reduction in cerebral compliance eventually will lead to an undesired increase in intracranial pressure, also known as hydrocephalus. As more fluid volume is added, a threshold is reached beyond which small increases in volume lead to dramatic and unhealthy increases in intracranial pressure.

A typical device to treat fluid conditions such as hydrocephalus is a ventricular catheter disclosed by Watson et al. in U.S. Pat. No. 5,738,666. In one embodiment, ventricular catheter 22 has a slit 60 in a distal tip 58. A terminal end 40 of a rigid introducer cannula 34 is inserted through the slit 60 during final placement of the ventricular catheter within a selected ventricle. A Tuohy-Borst adaptor 32 is secured to the proximal end of the introducer cannula 34. During set-up, a fiber-optic shaft 66 of an endoscope is advanced through the adaptor 32 and the cannula 34 until a fiber-optic terminal end 28 emerges past ventricular catheter terminal end 58 and aligns with introducer terminal end 40. Fiber-optic shaft 66 is then interlocked relative to introducer cannula 34. The aligned tips of the fiber-optic shaft 66 and the introducer cannula are then retracted proximally within catheter 22 during advancement through tissue until a selected ventricle is reached.

In other words, visualization does not occur during navigation of the Watson et al. catheter through the brain tissue and at least some of a selected ventricle. The doctor or other user is "blind" until the fiber-optic shaft is advanced through the slit in the ventricular catheter. Complications which may arise during placement of a ventricular catheter include injury to vascular structures such as the choroid plexus, injury to neurological structures, and improper positioning of the distal tip of the catheter.

There are a number of brain disorders that arise from neurotoxins or other pathogenic substances which can accumulate in cerebrospinal fluid. For example, it has long been recognized that aggregation of the protein amyloid-beta, which can be found in cerebrospinal fluid, contributes to the degenerative condition known as Alzheimer's disease. Microscopic damage to brain tissue leads to atrophy and a general decline in brain function known as dementia.

Delivery of a substance or certain wavelengths of optical radiation may be beneficial for some medical conditions. Introducing one or more compounds to treat Alzheimer's disease is described, for example, by DiMauro et al. in U.S. Patent Publication No. 2010/0286585. Introduction of red light through the cribriform plate portion of a nasal cavity to treat Alzheimer's disease is disclosed in U.S. Pat. No. 7,351,253 by DiMauro et al.

It is therefore desirable to have a simpler and more accurate device and technique for managing bodily fluids, especially cerebrospinal fluid.

SUMMARY OF THE INVENTION

An object of the present invention is to enable continuous visualization during insertion of a fluid management catheter in a patient, particularly within a fluid-filled region.

Another object of the present invention is to minimize exposure of the distal tip of an endoscope to tissue during placement of the catheter without impairing visualization.

This invention features a catheter having an elongated shaft with a distal end and a proximal end. The shaft defines at least one lumen extending substantially therethrough, the shaft further defining a plurality of drainage holes along a distal portion of the shaft, with the drainage holes in fluid communication with the lumen. The catheter further has a substantially transparent tip portion attached to the distal end of the shaft with an outer distal leading surface that is substantially rounded to assist insertion through tissue.

In a preferred embodiment, the tip portion defines at least one opening in fluid communication with (i) the shaft lumen, (ii) an irrigation lumen, or (iii) both the shaft lumen and the irrigation lumen. The irrigation lumen is defined by the shaft separately from the shaft lumen in some embodiments and, in other embodiments, is defined by independent structure such as a fiber-optic shaft or other optical conduit. In one embodiment, the opening is substantially arcuate.

In some embodiments, at least one substantially transparent insert is disposed along the distal portion of the shaft, and the shaft carries an optical conduit in optical communication with the at least one insert. The optical conduit is fixed in one embodiment and is removable in another embodiment. In one embodiment, the tip portion includes a wide angle lens such as a fisheye-type lens.

This invention may also be expressed as a method for managing fluid within a brain of a patient by selecting a catheter having an elongated shaft with a distal end and a proximal end, the shaft defining at least one lumen extending substantially therethrough, the shaft further defining a plurality of drainage holes along a distal portion of the shaft, and the drainage holes being in fluid communication with the lumen. The catheter further has a substantially transparent tip portion attached to the distal end of the shaft with an outer distal leading surface that is substantially rounded to assist insertion through tissue. The method further includes inserting the catheter through brain tissue to enter a selected ventricle, and visualizing through the tip portion of the catheter while positioning the tip portion within the selected ventricle.

In some embodiments, the tip portion defines at least one opening in fluid communication with one of the shaft lumen and an irrigation lumen defined by the shaft. The method further includes delivering fluid into the brain through at least the opening in the tip portion.

In other embodiments, the method includes placing a distal end of a fiber-optic shaft into the lumen of the catheter and against the tip portion to view, indirectly and substantially continuously through the tip portion, tissue within the selected ventricle. In certain embodiments, the method further includes removing the fiber-optic shaft from the catheter after the tip portion has been positioned at a desired location. In some embodiments, force is applied to the fiber-optic shaft to assist insertion of the distal tip through tissue. In yet other embodiments, therapeutic optical radiation is delivered through at least the tip portion.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a catheter having an elongated shaft with a distal end and a proximal end. The shaft defines at least one lumen extending substantially therethrough, the shaft further defining a plurality of drainage holes along a distal portion of the shaft, with the drainage holes in fluid communication with the lumen. The catheter further has a substantially transparent tip portion attached to the distal end of the shaft with an outer distal leading surface that is substantially rounded to assist insertion through tissue, preferably by blunt dissection to minimize trauma to the brain tissue.

Figure 1:
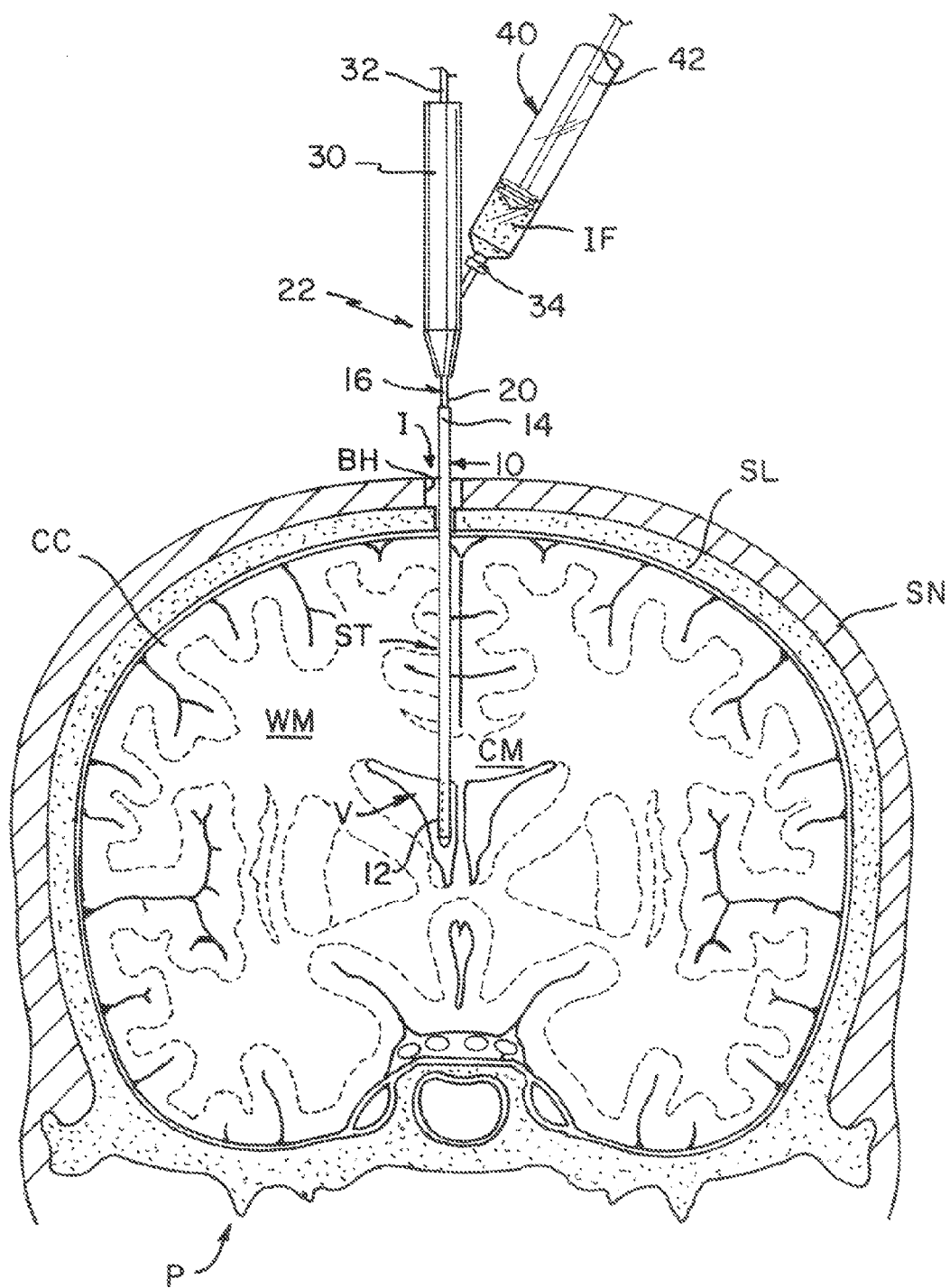
FIG. 1 is a partial cross-sectional coronal view of a patient showing a ventricular catheter according to the present invention being implanted within the brain according to one embodiment of the present invention.

The head of a patient P is illustrated in coronal cross-section in FIG. 1 with a ventricular catheter 10 according to the present invention inserted through incision I in soft tissue and skin SN and through burr hole BH at an upper region of skull SL. A distal portion 12 of catheter 10 is shown positioned within a lateral ventricle V after passing through cerebral cortex CC, white matter WM and corpus callosum CM along surgical tract ST formed by the insertion of catheter 10.

A fiber-optic shaft 20 is positioned within a lumen 16 extending through shaft 14 of catheter 10 to establish a visualization assembly 22. Housing 30 enables force to be applied by a surgeon or other user to fiber-optic shaft 20 as described in more detail below. Cable 32 optically connects fiber-optic shaft 20 with an optics module during insertion of catheter 10. In some constructions, cable 32 also delivers illuminating light during insertion and, in other constructions, delivers therapeutic optical radiation after insertion of catheter 10.

In this construction, fiber-optic shaft 20 also defines an irrigation lumen as described in more detail below. One suitable fiber-optic shaft with irrigation lumen is the NeuroPEN endoscope available from Medtronic PS Medical. Handle 30 has a luer-lock port 34 to which a syringe 40, with plunger 42, can be mated to deliver injection fluid IF such as a saline solution for irrigation or a mixture including one or more compounds for therapeutic purposes.

Figure 2:
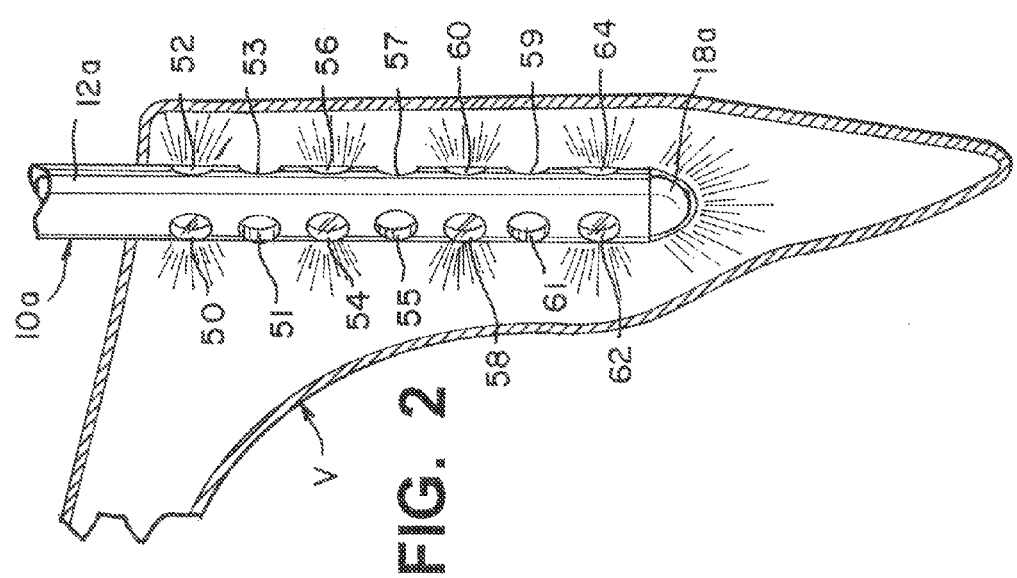
FIG. 2 is an enlarged side view of the distal portion of a ventricular catheter according to another embodiment of the present invention within a ventricle.

FIG. 2 illustrates one construction of a ventricular catheter 10a according to the present invention with a distal portion 12a positioned within a ventricle V and having substantially optically transparent inserts 50, 52, 54, 56, 58, 60, 62 and 64 as well as fluid management openings 51, 53, 55, 57, 59 and 61. One advantage of the illustrated configuration of alternating inserts and openings is that optical radiation can be directed over a large volume while still enabling withdrawal or delivery of fluid over a significant amount of the distal portion 12a.

In this construction, the inserts 50, 52 . . . 64 and distal tip 18a are formed of a medical grade PMMA (polymethyl methacrylate) such as FDA-approved Polycast PMMA, preferably with a low roughness value. To further minimize growth of cells or accumulation of substances on the PMMA substrates, the PMMA preferably is exposed to a gas plasma of a fluorinated carbon or otherwise treated in a manner similar to ophthalmic lenses. In some constructions, heparin surface modifications reduce adherent cells and debris. The catheter shaft 10 is formed of a silicone elastomer in one construction and is formed of other flexible, medical-grade polymers in other constructions. One or more antimicrobial agents may be coated onto the shaft 10 or incorporated into the shaft material during manufacture.

The pattern of projected optical radiation through distal tip 18a and the inserts 50, 52 . . . 64 is pre-determined by the curvature of the inner and outer surfaces of those elements. A plano-convex or bi-convex lens will converge or focus optical radiation, especially if the radiation is substantially collimated such as produced by a laser. A plano-concave or bi-concave lens will diverge or spread imaging and illumination over a larger area. Optical radiation is shown diverging through the inserts and the distal tip in FIG. 2 into the cerebral spinal fluid within ventricle V. In some constructions, the distal tip is configured to magnify images viewed through it, or provide a wide angle view such as a fisheye-type expanded view. A wide angle lens such as a fisheye-type lens is desirable to increase the field of view for a user while minimizing distortion. Different types of lenses can be utilized according to the present invention for inserts 50 . . . 64 and distal tip 18a such as lenses disclosed for ophthalmic implants by Grendahl and Isaacson et al. in U.S. Pat. Nos. 4,759,762 and 5,152,788, respectively, and for catheters by Farr et al. in U.S. Pat. No. 5,782,825. A rounded, substantially bullet-shaped outer surface is preferred for the distal tip to facilitate blunt dissection of tissue as the catheter is advanced through brain tissue. A distal tip according to the present invention provides an effective viewing lens larger than the inner diameter of the catheter and, therefore, larger than is possible for any endoscope insertable through the catheter.

The inserts and distal tip are secured to the shaft of the catheter with a biocompatible adhesive, an ultrasonic welding technique, or other suitable procedure. In some constructions, the distal tip has a proximally extending lead or post which mates with the inner diameter of the shaft 10a. In some constructions with at least one substantially transparent insert disposed along the distal portion of the shaft, an optical conduit is carried by the shaft in optical communication with the at least one insert. The optical conduit is fixed in one construction and is removable in another construction.

Figure 3:
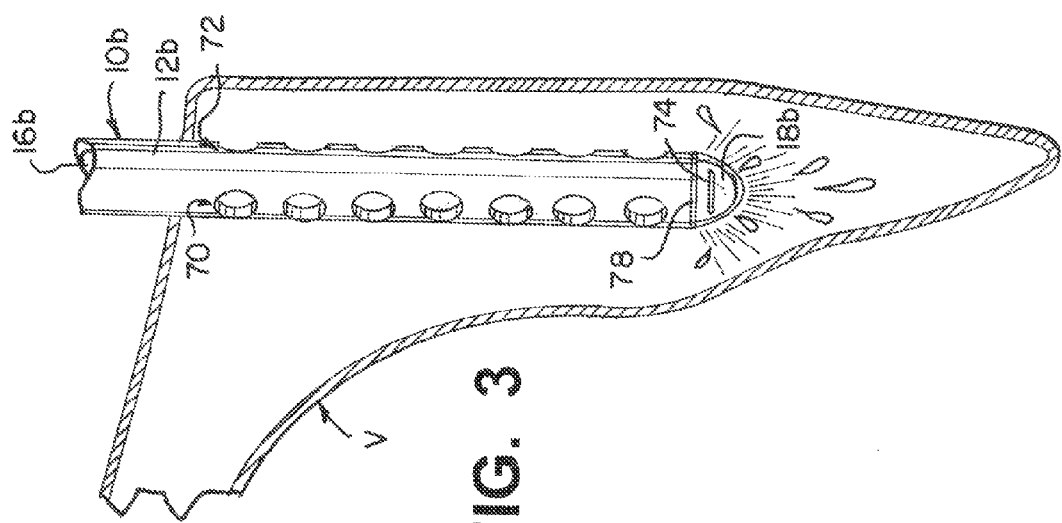
FIG. 3 is an enlarged side view of the distal portion of another embodiment of a ventricular catheter according to the present invention within a ventricle.
Figure 3A:
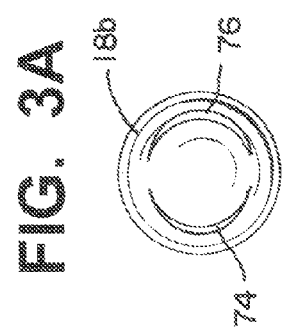
FIG. 3A is an enlarged end view of the distal tip of the catheter of FIG. 3.

Another construction of a ventricular catheter 10b is shown in FIGS. 3 and 3A. A distal portion 12b defines at least rows 70 and 72 of openings through which fluid enters into a central shaft lumen 16b and is withdrawn proximally. A distal tip 18b defines arcuate openings 74 and 76 through which irrigation fluid or therapeutic fluid can be directed. Having at least one opening in the distal tip 18b also enables cerebrospinal fluid or other bodily fluid to be selectively withdrawn from the distal-most region of catheter 10b, together with or independently of optical radiation being directed through tip 18b, according to physician preference. In this construction, distal portion 12b carries a radiographic marker 78 formed of a radiopaque material such as tantalum. Alternatively, a radiopaque material may be incorporated into the transparent material of one or more inserts shown in FIG. 2 and/or the transparent material of distal tips 10a, 10b.

Figure 4:
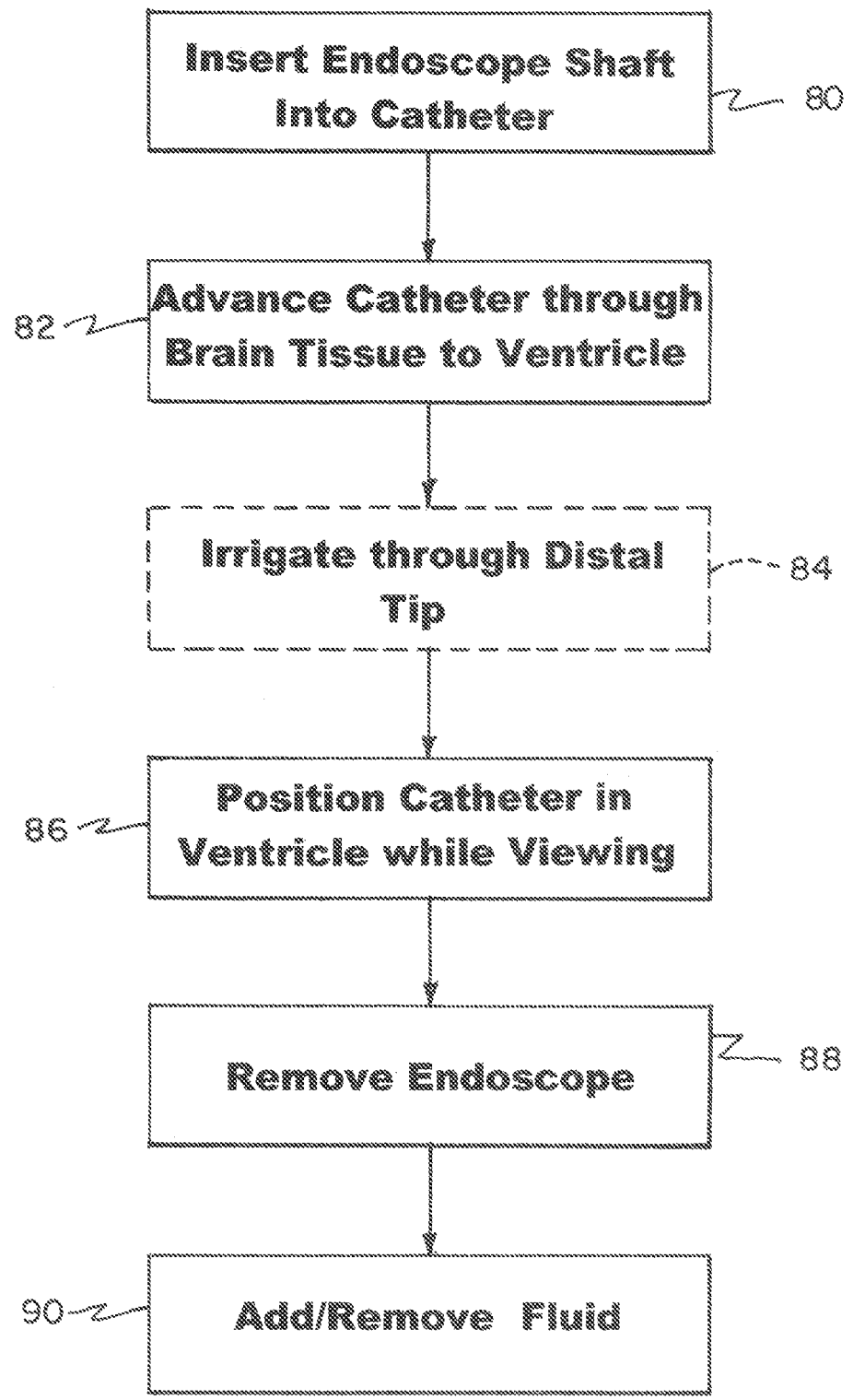
FIG. 4 is a flow chart of one implantation technique according to the present invention.

One procedure according to the present invention for fluid management within a brain of a patient is represented by the flow chart of FIG. 4. A shaft of an endoscopic device is inserted, step 80, into a lumen of a ventricular catheter according to the present invention to establish a visualization assembly. This assembly is established inside an operating room in one procedure and is established outside of the operating room in other procedures. The visualization assembly, referred to as the catheter in step 82, is advanced through brain tissue until a selected ventricle is reached. Step 84, shown in phantom, represents optional irrigation of at least a portion of the outer surface of the distal tip, such as for the ventricular catheter illustrated in FIGS. 3 and 3A. Irrigating through the distal tip flushes debris from the line of sight of the endoscope. Irrigation can also be utilized to maintain a positive pressure within the catheter to reduce ingress of cellular debris.

It is a realization of the present invention that enabling viewing through an optically transparent tip of a ventricular catheter when a selected ventricle is reached is likely to minimize damage to sensitive tissue during placement of the ventricular catheter, step 86. The viewing may be considered as indirect visualization through the optically transparent distal tip, which protects the endoscope shaft from direct contact with brain tissue during placement of the catheter. As noted above, complications which may arise during conventional placement of a ventricular catheter include injury to vascular structures such as the choroid plexus, injury to neurological structures, and improper positioning of the distal tip of the catheter.

Advancing the catheter through brain tissue, step 82, and positioning the catheter in a ventricle, step 86, preferably utilizes the endoscope shaft as a stylet. The distal tip of the catheter acts as a stop, that is, prevents axial translation of the endoscope shaft relative to the catheter, so that force applied to the endoscope shaft is directly transmitted to the distal tip to advance the catheter, preferably via blunt dissection of brain tissue.

Once the distal portion of the catheter is in a desired position the endoscope shaft is removed, step 88, and fluid is added and/or removed, step 90, according to surgeon preference and desired modality of treatment. In some techniques, therapeutic optical radiation is delivered through at least the distal tip. Utilizing a catheter having longitudinal inserts such as catheter 10a, FIG. 2, enables therapeutic optical radiation to be delivered through inserts 50, . . . 64 over a large volume of fluid.

Thus, while there have been shown, described, and pointed out fundamental novel features of the invention as applied to preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for managing fluid within a brain of a patient, comprising:
selecting a catheter having an elongated shaft with a distal end and a proximal end, the shaft defining a shaft lumen extending substantially therethrough, the shaft further defining a plurality of drainage holes along a distal portion of the shaft, the shaft further defining a plurality of optically transparent inserts along a distal portion of the shaft, the drainage holes being in fluid communication with the shaft lumen, the catheter further having a substantially transparent tip portion attached to the distal end of the shaft with an outer distal leading surface that is substantially rounded to assist insertion through tissue;
placing a distal end of a fiber-optic shaft into the shaft lumen of the catheter and against the tip portion to view, indirectly and substantially continuously through the Up portion, tissue within a selected ventricle;
inserting the catheter through tissue in the brain to enter the selected ventricle;
directing optical radiation from within the shaft through each of the plurality of optically transparent inserts; and
visualizing through the tip portion of the catheter while positioning the tip portion within the selected ventricle;

wherein the fiber optic shaft includes an irrigation lumen;
irrigating fluid to at least a portion of an outer surface of the tip portion through an opening in the tip portion;
withdrawing fluid from outside of said catheter through said plurality of drainage holes into the shaft lumen.

2. The method of claim 1 wherein the tip portion defines at least one opening in fluid communication with one of (i) the shaft lumen and (ii) the irrigation lumen separate from the shaft lumen.

3. The method of claim 1 further including removing the fiber-optic shaft from the catheter after the tip portion has been positioned at a desired location.

4. The method of claim 1 wherein inserting the catheter includes applying force to the fiber-optic shaft to assist insertion of the distal tip through tissue.

5. The method of claim 1 further including delivering therapeutic optical radiation through at least the tip portion.

6. The method of claim 1 further including the plurality of optically transparent inserts and the plurality of drainage holes being disposed in alternating order.

* * * * *